US009168238B2

(12) United States Patent
Jiang et al.

(10) Patent No.: US 9,168,238 B2
(45) Date of Patent: *Oct. 27, 2015

(54) LEVOTHYROXINE FORMULATIONS

(71) Applicant: FRESENIUS KABI USA, LLC, Lake Zurich, IL (US)

(72) Inventors: John Zhiqiang Jiang, Skokie, IL (US); Arunya Usayapant, Mundelein, IL (US); George Monen, Woodridge, IL (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/641,426

(22) Filed: Mar. 8, 2015

(65) Prior Publication Data

US 2015/0174246 A1 Jun. 25, 2015

Related U.S. Application Data

(63) Continuation of application No. 13/597,884, filed on Aug. 29, 2012, now Pat. No. 9,006,289.

(60) Provisional application No. 61/529,084, filed on Aug. 30, 2011.

(51) Int. Cl.
*A61K 31/198* (2006.01)
*A61K 47/26* (2006.01)
*A61K 9/00* (2006.01)
*A61K 9/19* (2006.01)
*A61K 47/02* (2006.01)
*A61K 47/10* (2006.01)

(52) U.S. Cl.
CPC ............. *A61K 31/198* (2013.01); *A61K 9/0019* (2013.01); *A61K 9/19* (2013.01); *A61K 47/02* (2013.01); *A61K 47/10* (2013.01); *A61K 47/26* (2013.01)

(58) Field of Classification Search
CPC ... A61K 31/198; A61K 47/26; A61K 9/0019; A61K 9/19
IPC ..................... A61K 31/198, 47/26, 9/0019, 9/19
See application file for complete search history.

(56) References Cited

U.S. PATENT DOCUMENTS

| | | | |
|---|---|---|---|
| 5,225,204 | A | 7/1993 | Chen et al. |
| 5,955,105 | A | 9/1999 | Mitra et al. |
| 6,936,274 | B2 | 8/2005 | Hanshew, Jr. et al. |
| 8,318,712 | B2 | 11/2012 | Pierres et al. |
| 9,006,289 | B2 * | 4/2015 | Jiang et al. ............ 514/567 |
| 2012/0190748 | A1 | 7/2012 | Treasurer |

FOREIGN PATENT DOCUMENTS

JP 2002284679 10/2002

OTHER PUBLICATIONS

U.S. Appl. No. 14/658,058, filed Mar. 2015, Jiang et al.*
APP Pharmaceuticals, LLC, "Highlights of Prescribing Information," 2011, pp. 1-11.
APP Pharmaceuticals, LLC, "Levothyroxine Sodium for Injection", 2008, pp. 1-3.
Baheti, et al, "Excipients used in lyophilization of small molecules," "J. Excipients and Food Chem.," 2010, pp. 41-54, vol. 1, No. 1.
Bedford Laboratories, "Levothyroxine Sodium for Injection," 2003, pp. 1-2.
Schering Corporation, "Leventa—levothyroxine sodium solution," 2010, pp. 1-3.
Vidyya Medical News Service, "Synthroid, The Most Commonly Prescribed Medication in the US," 2000, pp. 1-11.
International Searching Authority, "International Search Report and Written Opinion for PCT/US2012/052838," Nov. 16, 2012, Publisher: European Patent Office, Published in: EP.
Collier, et al., "Influence of Formulation and Processing Factors on Stability of Levothyroxine Sodium Pentahydrate," "APPS PharmSiTech," May 8, 2010, pp. 818-825, vol. 11, No. 2.
Rowe, et al., "Mannitol," "Handbook of Pharmaceutical Excipients," 2006, pp. 449-453.
Beth D. Herman et al., The Effect of Bulking Agent on the Solid-State Stability of Freeze-Dried Methylprednisolone Sodium Succinate, Pharmaceutical Research, vol. 11, No. 10, pp. 1467-1473 (May 11, 1994).
Alexandra I. Kim et al., The physical state of mannitol after freeze-drying: effects of mannitol concentration, freezing rate, and a noncrystallizing cosolute, Journal of Pharmaceutical Sciences, vol. 87, No. 8, pp. 931-935 (May 11, 1998).
Searles, JA., "Freezing and Annealing Phenomena in Lyophilization," Freeze Drying/Lyophilization of Pharmaceutical and Biological Products, 3rd Edition. Ed. Louis Rey, Ed. Joan C. May. London: Informa Healthcare, 2010, 52-81.
Won, CM., "Kinetics of Degradation of Levothyroxine in Aqueous Solution and in Solid State," Pharm. Res., 9: 131-137 (1992).
SYNTHROID® Injection (levothyroxine sodium), Physicians' Desk Reference, Medical Economics, 1970 (3 pages).
LEVOTHROID® (levothyroxine sodium) For Injection, Physicians' Desk Reference, Medical Economics, 1986 (3 pages).
US Department of Health and Human Services, Food and Drug Administration, Center for Drug Evaluation and Research, Synthroid® (Levothyroxine Sodium tablets, USP) Application No. 21-402, 2002 (17 pages).
Gieseler et al., "Influence of Common Excipients on the Crystalline Modification of Freeze-Dried Mannitol," Pharmaceutical Technology, 3(32) (Mar. 2, 2008) (4 pages).
Kazemifard et al., "Identification and Quantitation of Sodium-Thyroxine and its Degradation Products by LC Using Electrochemical and MS Detection," J. Pharm. Biomed. Anal., 25(5-6): 697-711 (Jul. 2001) (15 pages).
Patel et al., "The Effect of Excipients on the Stability of Levothyroxine Sodium Pentahydrate Tablets," Int. J. Pharm., 264(1-2), pp. 35-43 (Oct. 2, 2003) (9 pages).

(Continued)

*Primary Examiner* — Kara R McMillian
(74) *Attorney, Agent, or Firm* — Baker & Hostetler LLP

(57) ABSTRACT

A levothyroxine composition includes levothyroxine sodium and mannitol. The composition is a lyophilized solid. The composition may include from 100 to 500 micrograms levothyroxine sodium and from 2 to 4 milligrams mannitol.

30 Claims, 3 Drawing Sheets

(56) References Cited

OTHER PUBLICATIONS

Stadalman et al., "Stability of Levothyroxine Sodium 0.4 microg/mL in 0.9% Sodium Chloride Injection," Prog. Transplant., 19(4), pp. 354-357 (Dec. 2009) (4 pages).

Strong et al., "Stability of Levothyroxine in Sodium Chloride for IV Administration," Can. J. Hosp. Pharm., 63(6), p. 437-443 (Nov. 2010) (7 pages).

United States Pharmacopeia and National Formulary (Revision Bulletin) Rockville, MD: United States Pharmacopeia Convention; Levothyroxine pp. 1-3 (Oct. 1, 2010) (3 pages).

US Department of Health and Human Services, Food and Drug Administration, Center for Drug Evaluation and Research, "Chemistry Review(s)," Levothyroxine Sodium for Injection, Application No. 202231, Jun. 2011 (41 pages).

US Department of Health and Human Services, Food and Drug Administration, Center for Drug Evaluation and Research, "Summary Review," Levothyroxine Sodium for Injection, Application No. 202231, Jun. 2011 (12 pages).

US Department of Health and Human Services, Food and Drug Administration, Center for Drug Evaluation and Research, "Guidance for Industry: Q1A(R2) Stability Testing of New Drug Substances and Products," Revision 2, Nov. 2003 (25 pages).

US Department of Health and Human Services, Food and Drug Administration, Center for Drug Evaluation and Research, "Guidance for Industry: Q8(R2) Pharmaceutical Development," Revision 2, Nov. 2009 (29 pages).

Handbook of Pharmaceutical Manufacturing Formulations: Sterile Products 2nd Edition, vol. 6 (Niazi ed.), pp. 315-317 (Sep. 2009), ISBN: 9781420081305 (5 pages).

Intravenous Therapy: A Comprehensive Application of Intravenous Therapy and Medication Administration (Nentwich ed.), pp. 357-358 (Mar. 1990), ISBN: 0867204192 (4 pages).

Delmar Nurse's Drug Handbook, 2009 Edition (Spratto et al. ed.), pp. 967-969, ISBN-13: 9781428361065 (5 pages).

LEVO-T® (levothyroxine sodium tablets, USP) Prescribing Information, 2002 (17 pages).

LEVOXYL® (levothyroxine sodium tablets, USP) Prescribing Information, 2001 (12 pages).

SYNTHROID® (levothyroxine sodium tablets, USP) Prescribing Information, 2002 (19 pages).

THYRO-TABS® (levothyroxine sodium tablets, USP) Prescribing Information, 2002 (14 pages).

UNITHROID® (levothyroxine sodium tablets, USP) Prescribing Information, 2000 (14 pages).

* cited by examiner

LEVOTHYROXINE FORMULATIONS

REFERENCE TO RELATED APPLICATIONS

This application is a continuation of U.S. patent application Ser. No. 13/597,884, filed Aug. 29, 2012, which claims the benefit of U.S. Provisional Application No. 61/529,084, filed Aug. 30, 2011, which are both incorporated by reference in their entirety.

BACKGROUND

A healthy thyroid produces hormones that regulate multiple metabolic processes and that play important roles in growth and development, in maturation of the central nervous system and bone including augmentation of cellular respiration and thermogenesis, and in metabolism of proteins, carbohydrates and lipids. The thyroid accomplishes its regulation functions by producing the hormones L-triiodothyronine (liothyronine; T3) and L-thyroxine (levothyroxine; T4).

Thyroid hormones are believed to exert their physiologic actions through control of DNA transcription and protein synthesis. It is presently believed that the T3 and T4 hormones diffuse into the cell nucleus and bind to thyroid receptor proteins attached to DNA. This hormone nuclear receptor complex then activates gene transcription and synthesis of messenger RNA and cytoplasmic proteins. The physiological actions of thyroid hormones are believed to be produced predominantly by T3, approximately 80% of which is derived from T4 by deiodination in peripheral tissues.

Both T3 and T4 are stored in the thyroid as thyroglobulin adducts with serum proteins. Once secreted by the thyroid, T3 and T4 primarily exist in the circulatory system as their thyroglobulin adducts, and are in equilibrium with small amounts (<1%) of the unbound hormones, which are the metabolically active species. T4 has higher serum levels, slower metabolic clearance, and a longer half-life than T3, which may be due to the higher affinity of serum proteins for T4 compared to T3.

A patient who has had their thyroid gland removed, or whose thyroid gland functions at an undesirably low level (hypothyroidism), may be treated by administration of a daily maintenance dose of 50-100 micrograms (µg) of levothyroxine sodium. A patient in need of additional intervention may be treated by administration of an initial dose of 200-500 µg or 300-500 µg of levothyroxine sodium and/or with a $2^{nd}$ day dose of 100-300 µg of levothyroxine sodium. Formal names for levothyroxine sodium include 4-(4-hydroxy-3,5-diiodophenoxy)-3,5-diiodo-L-phenylalanine sodium, and L-tyrosine-O-(4-hydroxy-3,5-diiodophenyl)-3,5-diiodo-monosodium salt. The chemical structure of levothyroxine sodium is shown in FIG. 1.

Administration of levothyroxine sodium provides T4 to a patient. Once absorbed by the organism, the administered T4 behaves identically to T4 that otherwise would be secreted by the thyroid gland of the patient, and binds to the same serum proteins, providing a supply of circulating T4-thyroglobulin in the patient. The administered T4 may be deiodinated in vivo to T3. As a result, a patient receiving appropriate doses of levothyroxine sodium will exhibit normal blood levels of T3, even when the patient's thyroid gland has been removed or is not functioning.

Levothyroxine sodium for injection is a sterile lyophilized product for parenteral administration of levothyroxine sodium for thyroid replacement therapy. Levothyroxine sodium for injection is particularly useful when thyroid replacement is needed on an urgent basis, for short term thyroid replacement, and/or when oral administration is not possible, such as for a patient in a state of myxedema coma.

Conventional formulations of levothyroxine sodium for injection are preservative-free lyophilized powders containing synthetic crystalline levothyroxine sodium and the excipients mannitol, tribasic sodium phosphate, and sodium hydroxide. These conventional formulations typically contain 10 milligrams (mg) of mannitol, 700 µg of tribasic sodium phosphate, and either 200 µg or 500 µg of levothyroxine sodium. Administration of the conventional formulation involves reconstitution of the lyophilized powder in 5 milliliters (mL) of 0.9% sodium chloride injection (USP), to provide injectable solutions having levothyroxine sodium concentrations of 40 micrograms per milliliter (µg/mL) or 100 µg/mL, respectively.

It is desirable to provide a new formulation of levothyroxine sodium that can further improve the stability of the levothyroxine. Preferably a new formulation of levothyroxine sodium would have acceptable stability above room temperature for an extended period of time. It is also desirable for the new formulation to be convenient to store, to reconstitute, and to administer to a patient.

SUMMARY

A composition is provided that includes from 100 to 500 micrograms of levothyroxine sodium, and from 1 to 5 milligrams mannitol. The composition is a solid.

A composition is provided that includes from 100 to 200 micrograms of levothyroxine sodium, and mannitol. The mass ratio of mannitol to levothyroxine sodium is at most 40:1, and the composition is a solid.

A composition is provided that includes about 500 micrograms of levothyroxine sodium, and mannitol. The mass ratio of mannitol to levothyroxine sodium is at most 10:1, and the composition is a solid.

A plurality of compositions is provided, where each composition includes from 100 to 500 micrograms of levothyroxine sodium and from 1 to 5 milligrams mannitol, and each composition is a solid. The amount of levothyroxine sodium in each composition spans the range of 100 to 500 micrograms. The amount of mannitol is substantially the same in each composition. When the plurality of compositions is stored at 25° C., at most 0.20% of the levothyroxine sodium in each composition is converted to liothyronine over a period of 12 months.

A solid composition is provided, which is formed by a method that includes combining ingredients to form a liquid mixture, and lyophilizing the liquid mixture. The ingredients include a solvent, levothyroxine sodium, mannitol, and substantially no tribasic sodium phosphate.

A solid composition is provided, which is formed by a method that includes combining ingredients to form a liquid mixture, and lyophilizing the liquid mixture. The ingredients include a solvent, levothyroxine sodium, mannitol and dibasic sodium phosphate. The mass ratio of mannitol to levothyroxine sodium in the liquid mixture is at most 40:1.

To provide a clear and more consistent understanding of the specification and claims of this application, the following definitions are provided.

The term "mass ratio" of two substances means the mass of one substance (S1) relative to the mass of the other substance (S2), where both masses have identical units, expressed as S1:S2.

The term "lyophilizing" means removing from a solution or an emulsion one or more substances having the lowest boiling points by freezing the solution or emulsion and applying a vacuum to the frozen mixture.

The term "spans the range", with regard to a range of the amount of a substance in a plurality of compositions, means that at least one of the compositions contains the substance in an amount corresponding to the lowest end of the range, at least one of the compositions contains the substance in an amount corresponding to the highest end of the range, and the remaining compositions, if any, contain the substance in an amount within the range. For example, in a plurality of compositions in which the amount of levothyroxine sodium spans the range of 100-500 µg, at least one of the compositions contains 100 µg levothyroxine sodium, at least one of the other compositions contains 500 µg levothyroxine sodium, and the remaining compositions, if any, contain from 100 µg to 500 µg levothyroxine sodium.

BRIEF DESCRIPTION OF THE DRAWINGS

The invention can be better understood with reference to the following drawing and description. The components in the figure are not necessarily to scale and are not intended to accurately represent molecules or their interactions, emphasis instead being placed upon illustrating the principles of the invention.

DETAILED DESCRIPTION

Figure 1:
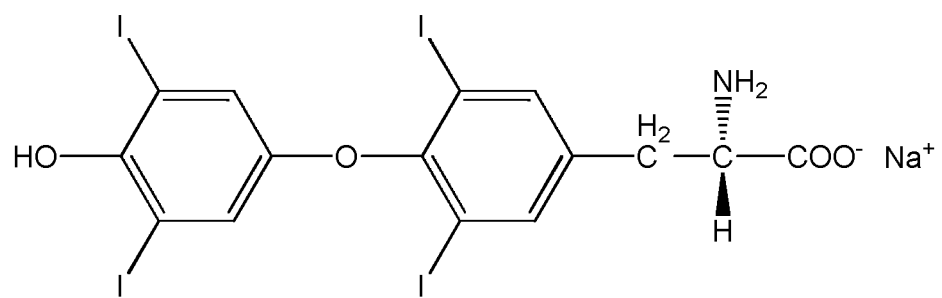
FIG. 1 depicts a chemical structure of levothyroxine sodium.

Lyophilized levothyroxine sodium compositions that include less mannitol than conventional compositions can protect levothyroxine from degradation at temperatures of 25° C. and higher. These compositions also can maintain a consistent level of levothyroxine over a wide range of dosages. Reconstitution of the lyophilized compositions with a carrier liquid can yield injectable liquids having ingredients that are more acceptable than those in conventional compositions.

A levothyroxine composition may include levothyroxine sodium, mannitol, and optionally one or more other substances, where the composition is a solid. Improved stability of levothyroxine can be achieved by lowering the mass of mannitol and/or the mass ratio of mannitol to levothyroxine sodium in the composition to a level below that of conventional levothyroxine compositions. Conventional levothyroxine compositions include 10 milligrams (mg) mannitol and either 200 or 500 micrograms (µg) levothyroxine sodium, corresponding to mass ratios of mannitol to levothyroxine sodium (M:L) of 50:1 and 20:1, respectively. In contrast, improved stability of levothyroxine can be obtained in compositions having either 200 or 500 µg levothyroxine sodium by lowering the amount of mannitol to 1 to 5 milligrams, corresponding to M:L ratios of from 5:1 to 25:1 and from 2:1 to 10:1, respectively.

Solid levothyroxine compositions may be prepared by forming a liquid mixture containing a solvent, levothyroxine sodium and mannitol, and lyophilizing the liquid mixture. Forming a liquid mixture for use in preparing the solid composition may include combining ingredients including a solvent, levothyroxine sodium and mannitol. The ingredients also may include a phosphate buffer; however the ingredients preferably do not include tribasic sodium phosphate.

A solid composition that includes levothyroxine sodium and mannitol may include from 25 to 1,000 µg levothyroxine sodium. Preferably the composition includes from 50 to 750 µg levothyroxine sodium, or from 100 to 500 µg levothyroxine sodium. The amount of levothyroxine sodium in the composition may be an amount sufficient for a single initial dose of levothyroxine sodium, an amount sufficient for a single $2^{nd}$ day dose of levothyroxine sodium, or an amount sufficient for a daily maintenance dose of levothyroxine sodium. The amount of levothyroxine sodium in the composition may be a different therapeutic amount. For example, the amount of levothyroxine sodium in the composition may be an amount sufficient for half of a single initial dose, half of a single $2^{nd}$ day dose, or half of a daily maintenance dose. Presently preferred amounts of levothyroxine sodium in the composition include about 100 µg, about 200 µg, and about 500 µg.

A solid composition that includes levothyroxine sodium and mannitol may include one or more other substances. Non-limiting examples of other substances include bulking agents, carriers, diluents, fillers, salts, buffers, stabilizers, solubilizers, preservatives, antioxidants, and tonicity contributors. Substances that may be useful in formulating pharmaceutically acceptable compositions, and methods of forming such compositions, are described for example in Remington: The Science and Practice of Pharmacy, 20th Ed., ed. A. Gennaro, Lippincott Williams & Wilkins, 2000, and in Kibbe, "Handbook of Pharmaceutical Excipients,"$3^{rd}$ Edition, 2000.

A solid composition that includes levothyroxine sodium and mannitol may be prepared by forming a liquid mixture containing a solvent, levothyroxine sodium and mannitol, and lyophilizing the liquid mixture. Forming a liquid mixture for use in preparing the solid composition may include combining ingredients including the solvent, levothyroxine sodium and mannitol. The ingredients used to form the liquid mixture may include a phosphate buffer; however the ingredients preferably do not include tribasic sodium phosphate. In one example, the ingredients used to form the liquid mixture include a phosphate buffer other than tribasic sodium phosphate, such as dibasic sodium phosphate ($Na_2HPO_4$) or monobasic sodium phosphate ($NaH_2PO_4$). The amount of phosphate buffer in the ingredients may be an amount sufficient to provide a beneficial pH buffering effect in the liquid mixture. Preferably the ingredients used to form the liquid mixture include from 100 to 800 µg, from 200 to 700 µg, from 300 to 700 µg, or from 400 to 600 µg dibasic sodium phosphate. Dibasic sodium phosphate may be added as a hydrate, such as dibasic sodium phosphate heptahydrate.

Forming the liquid mixture for use in preparing the solid composition may further include adding a base to the liquid mixture to provide a desired pH in the mixture, where the base is different from any buffers present in the composition, such as a phosphate buffer. The amount of the base added to the liquid mixture may be an amount sufficient to provide a liquid mixture pH in the range of 10.5 to 12.5 or from 11 to 12. The amount of the base may be an amount sufficient to provide a pH in the range of 9.5 to 11.5 or of 10 to 11 when a solid composition formed from the liquid mixture is subsequently reconstituted in 5 mL of 0.9% aqueous sodium chloride (USP). Presently preferred bases include sodium hydroxide.

A solid composition that includes levothyroxine sodium and mannitol may include from 25 µg to less than 10 mg mannitol. Preferably the composition includes from 0.1 to 7 mg mannitol, from 1 to 5 mg mannitol, from 2 to 4 mg mannitol, or from 2.9 to 3.1 mg mannitol. The amount of mannitol in the composition may be an amount sufficient to provide a beneficial bulking effect to the solid composition, while maintaining a M:L ratio less than 50:1, and preferably of 40:1 or less. For example, a solid composition that includes levothyroxine sodium and mannitol may have a M:L ratio less than 50:1, or at most 40:1. Preferably the composition has a M:L ratio of from 1:1 to 40:1, from 5:1 to 35:1, or from 6:1 to 30:1. Presently preferred M:L ratios include about 6:1, about 15:1 and about 30:1. For compositions that include less than 500 µg levothyroxine sodium, the mass ratio of mannitol to levothyroxine sodium preferably is at most 40:1. For compositions that include at least 500 µg levothyroxine sodium, the mass ratio of mannitol to levothyroxine sodium preferably is at most 10:1.

It has been discovered that, in a solid composition that includes levothyroxine sodium and mannitol, the stability of levothyroxine may be improved by lowering the amount of mannitol in the composition to a level below that of conventional compositions. Conventional levothyroxine compositions include either 200 or 500 µg levothyroxine sodium, and include 10 mg mannitol. In contrast, levothyroxine may have improved stability at room temperature and at elevated temperatures when present in solid compositions that include 100, 200 or 500 µg levothyroxine sodium and include less than 10 mg mannitol.

The stability of levothyroxine was analyzed for solid compositions that contained 100 µg levothyroxine sodium and from 2 mg to 10 mg mannitol. The solid compositions were formed by combining water, the levothyroxine sodium, the mannitol, and 500 µg dibasic sodium phosphate to form liquid mixtures, and then adding sodium hydroxide to provide a pH of about 11.8. Water for injection (USP) was added to each liquid mixture as needed to provide total volumes of 1 milliliter (mL). The liquid mixtures were lyophilized to provide solid compositions, which were then stored in amber tinted vials at temperatures of 40° C. or 55° C. The stability of the levothyroxine in the solid compositions at different temperatures was determined by measuring the amount of liothyronine (T3) in each composition over time, as T3 is a degradation product of levothyroxine (T4). The results of these measurements are listed in Table 1, below.

The results listed in Table 1 show that levothyroxine was more stable in the compositions containing less than 10 mg mannitol than in the composition containing a conventional amount of mannitol of 10 mg. The compositions having improved stability contained 4 mg, 3 mg or 2 mg mannitol, whereas the least stable composition contained a conventional amount of mannitol of 10 mg. The compositions having improved stability also had M:L ratios of at most 40:1, whereas the M:L ratio of the composition containing a conventional amount of mannitol was 100:1.

As shown in Table 1, during storage at 40° C. the amount of T3 in the composition containing 10 mg mannitol varied from 0.30% to 0.57% over a period of from 1 to 3 months, a range of approximately 90% [90.0%=100%×(0.57−0.30)/0.30]. In contrast, the amount of T3 in the compositions containing from 2 mg to 4 mg mannitol remained relatively stable under the same conditions, varying only by approximately 6% [5.6%=100%×(0.19−0.18)/0.18]. In the compositions containing 2 to 4 mg mannitol, at most 0.19% of the levothyroxine sodium was converted to liothyronine when stored at 40° C. over a period of 3 months.

As shown in Table 1, the compositions containing less than 10 mg mannitol maintained the stability of levothyroxine when stored at an even higher temperature of 55° C. During storage at 55° C. over a period of from 2 to 4 weeks, the amount of T3 in the compositions containing from 2 mg to 4 mg mannitol varied only by approximately 6% [5.6%=100%×(0.19−0.18)/0.18]. In the compositions containing 2 to 4 mg mannitol, at most 0.19% of the levothyroxine sodium was converted to liothyronine when stored at 55° C. over a period of 4 weeks.

The surprising and unexpected improvement in levothyroxine stability in a solid composition upon lowering the amount of mannitol in the composition also was observed in solid compositions that contained more than 100 µg levothyroxine sodium. The stability of levothyroxine was analyzed for solid compositions that contained from 100 µg to 500 µg levothyroxine sodium and 3 mg mannitol. The solid compositions were formed by combining water, the levothyroxine sodium, the mannitol, and 500 µg dibasic sodium phosphate to form liquid mixtures, and then adding sodium hydroxide to provide a pH of about 11.8. Water for injection (USP) was added to each liquid mixture as needed to provide total volumes of 1 mL. The liquid mixtures were lyophilized to provide solid compositions, which were then stored in amber tinted vials at temperatures of 25° C. or 40° C. The stability of the levothyroxine in the solid compositions at different temperatures was determined by measuring the amount of T3 in each composition over time, as described above. The results of these measurements are listed in Table 2, below. Each entry in this table represents an average of 3 measurements.

TABLE 1

Stability of levothyroxine in solid compositions containing different amounts of mannitol.

| Levothyroxine Sodium: | 100 µg | 100 µg | 100 µg | 100 µg |
| Dibasic Sodium Phosphate: | 500 µg | 500 µg | 500 µg | 500 µg |
| Mannitol: | 10 mg | 4 mg | 3 mg | 2 mg |
| M:L ratio: | 100:1 | 40:1 | 30:1 | 20:1 |

| Time | Temp. | | % T3 | | |
| --- | --- | --- | --- | --- | --- |
| 0 | — | 0.17 | 0.22 | 0.22 | 0.22 |
| 1 month | 40° C. | 0.34 | 0.19 | 0.18 | 0.18 |
| 2 months | | 0.30 | 0.18 | 0.18 | 0.19 |
| 3 months | | 0.57 | 0.18 | 0.18 | 0.18 |
| 2 weeks | 55° C. | — | 0.18 | 0.18 | 0.19 |
| 4 weeks | | — | 0.19 | 0.18 | 0.19 |

TABLE 2

Stability of levothyroxine in solid compositions containing different amounts of levothyroxine sodium and 3 mg mannitol.

| Levothyroxine Sodium: | 100 µg | 200 µg | 500 µg |
| Dibasic Sodium Phosphate: | 500 µg | 500 µg | 500 µg |
| Mannitol: | 3 mg | 3 mg | 3 mg |
| M:L ratio: | 30:1 | 15:1 | 6:1 |

| Time (mo.) | Temperature | | % T3 | |
| --- | --- | --- | --- | --- |
| 0 | — | 0.12 | 0.12 | 0.12 |
| 1 | 40° C. | 0.13 | 0.13 | 0.13 |
| 2 | | 0.13 | 0.13 | 0.14 |
| 3 | | 0.13 | 0.13 | 0.13 |
| 6 | | 0.13 | 0.14 | 0.13 |
| 3 | 25° C. | 0.13 | 0.13 | 0.13 |
| 6 | | 0.12 | 0.12 | 0.12 |
| 9 | | 0.13 | 0.13 | 0.13 |
| 12 | | 0.12 | 0.12 | 0.12 |

The results listed in Table 2 show that levothyroxine was stable at room temperature and at an elevated temperature of 40° C. when present at a variety of amounts, in solid compositions that included only 3 mg mannitol. The compositions containing 100 µg, 200 µg or 500 µg levothyroxine sodium and having improved stability contained 3 mg mannitol, whereas conventional levothyroxine compositions that contain 200 µg or 500 µg levothyroxine sodium include 10 mg mannitol. The composition containing 200 µg levothyroxine sodium and having improved stability had a M:L ratio of only 15:1, whereas the M:L ratio of a conventional composition containing 200 µg levothyroxine sodium is 50:1. The composition containing 500 µg levothyroxine sodium and having improved stability had a M:L ratio of only 6:1, whereas the M:L ratio of a conventional composition containing 500 µg levothyroxine sodium is 20:1.

As shown in Table 2, during storage at 25° C. the amount of T3 in the compositions containing 3 mg mannitol varied only by approximately 8% over a period of from 3 to 12 months [8.3%=100%×(0.13−0.12)/0.12)]. A similar variation in the amount of T3 was observed when the same compositions were stored at an elevated temperature of 40° C. over a period of from 1 to 6 months [7.7%=100%×(0.14−0.13)/0.13)].

Solid compositions that include levothyroxine sodium and mannitol preferably can protect levothyroxine from degradation for a year or longer at room temperature (25° C.), and for 6 months or longer at elevated temperatures. Referring to Table 2, each of the listed solid compositions maintained the level of T3 impurity below 0.15% for one year at 25° C. and for 6 months at 40° C. As shown in Table 2, in all of the compositions listed, at most 0.13% of the levothyroxine sodium was converted to liothyronine when stored at 25° C. over a period of 12 months. Similarly, in all of the compositions listed, at most 0.14% of the levothyroxine sodium was converted to liothyronine when stored at 40° C. over a period of 3 months or 6 months.

Preferably, when a solid composition that includes levothyroxine sodium and mannitol is stored at 25° C., at most 0.20% of the levothyroxine sodium is converted to liothyronine (T3) over a period of 12 months. Preferably, when a solid composition that includes levothyroxine sodium and mannitol is stored at 25° C., at most 0.15% or at most 0.14% of the levothyroxine sodium is converted to liothyronine over a period of 12 months.

Preferably, when a solid composition that includes levothyroxine sodium and mannitol is stored at 40° C., at most 0.20% of the levothyroxine sodium is converted to liothyronine over a period of 3 months. Preferably, when a solid composition that includes levothyroxine sodium and mannitol is stored at 40° C., at most 0.15% of the levothyroxine sodium is converted to liothyronine over a period of 3 months or over a period of 6 months. Preferably, when a solid composition that includes levothyroxine sodium and mannitol is stored at 40° C., at most 0.14% of the levothyroxine sodium is converted to liothyronine over a period of 3 months or over a period of 6 months.

Preferably, when a solid composition that includes levothyroxine sodium and mannitol is stored at 55° C., at most 0.20% of the levothyroxine sodium is converted to liothyronine over a period of 4 weeks. Preferably, when a solid composition that includes levothyroxine sodium and mannitol is stored at 55° C., at most 0.19% of the levothyroxine sodium is converted to liothyronine over a period of 4 weeks.

The results listed in Table 2 also show that levothyroxine was stable at room temperature and at an elevated temperature of 40° C. across a dosage range of 100 to 500 µg levothyroxine sodium. While the amount of levothyroxine sodium spanned the range of 100 µg to 500 µg, the amount of mannitol and phosphate buffer were substantially the same for each composition. Surprisingly, there was no significant difference in the initial T3 levels between these solid compositions, even though the amount of levothyroxine sodium in the compositions varied from 100 µg to 500 µg. Moreover, there was no significant difference in the T3 levels between the solid compositions over time, either at room temperature or at an elevated temperature. As shown in Table 2, in the plurality of compositions listed, at most 0.13% of the levothyroxine sodium in each of the compositions was converted to liothyronine when stored at 25° C. over a period of 12 months, and at most 0.14% of the levothyroxine sodium in each of the compositions was converted to liothyronine when stored at 40° C. over a period of 3 months or 6 months.

Solid compositions that include levothyroxine sodium and mannitol preferably can maintain a consistent level of pure levothyroxine, regardless of the concentration of the levothyroxine sodium in the composition. Preferably, when a plurality of solid compositions that include levothyroxine sodium and mannitol are stored at 25° C., where the amount of levothyroxine sodium spans the range of 100 µg to 500 µg and the amount of mannitol and any optional buffer are substantially the same for each composition, at most 0.20% of the levothyroxine sodium in each of the solid compositions is converted to liothyronine over a period of 12 months. Preferably, when a plurality of solid compositions that include levothyroxine sodium and mannitol are stored at 25° C., where the amount of levothyroxine sodium spans the range of 100 µg to 500 µg and the amount of mannitol and any optional buffer are substantially the same for each composition, at most 0.15% or at most 0.14% of the levothyroxine sodium in each of the solid compositions is converted to liothyronine over a period of 12 months. Preferably, when a plurality of solid compositions that include levothyroxine sodium and mannitol are stored at 40° C., where the amount of levothyroxine sodium spans the range of 100 µg to 500 µg and the amount of mannitol and any optional buffer are substantially the same for each composition, at most 0.15% or at most 0.14% of the levothyroxine sodium in each of the solid compositions is converted to liothyronine over a period of 3 months or over a period of 6 months.

Figure 2:
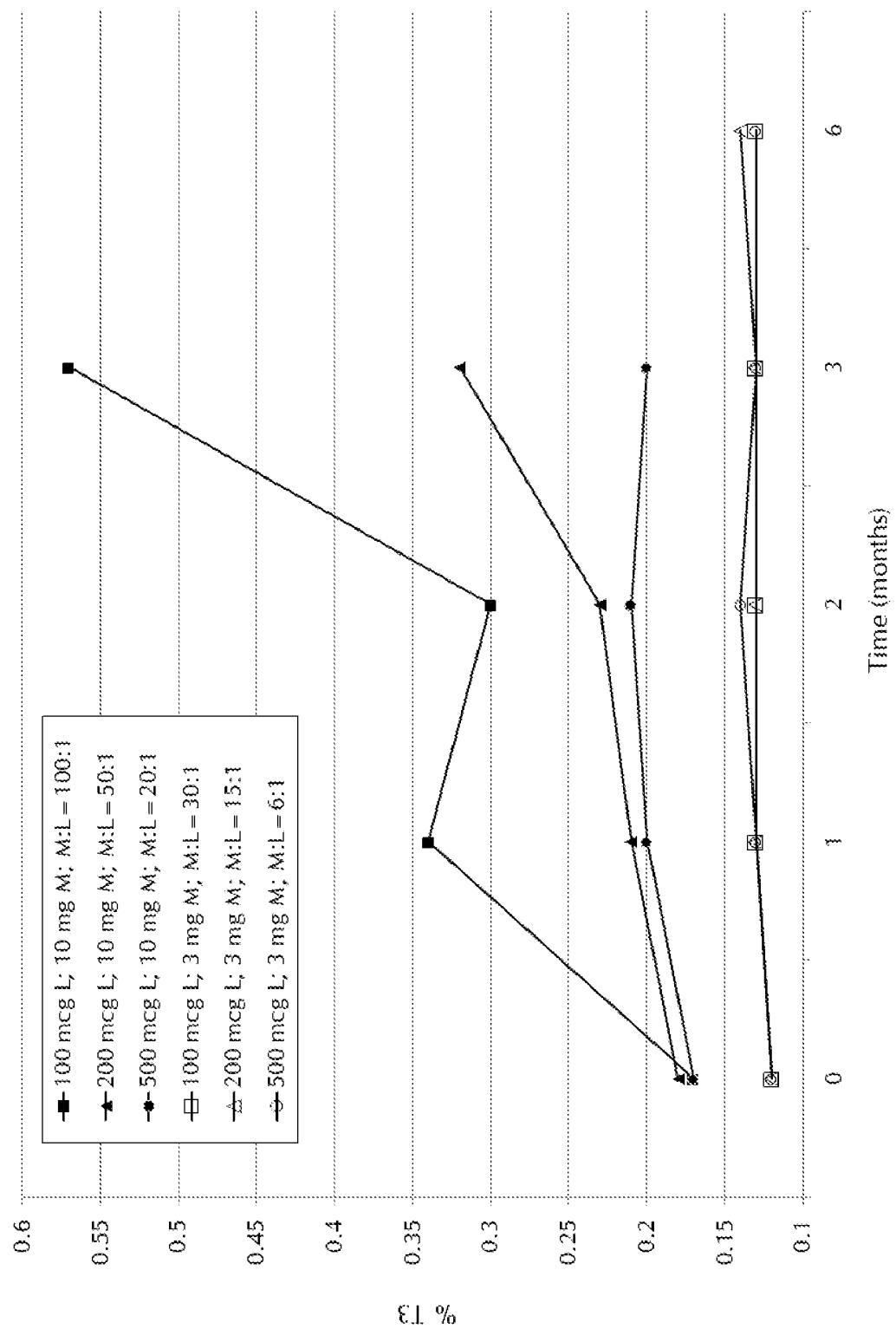
FIG. 2 depicts graphs of the amount of liothyronine (T3) impurity over time at 40° C. for compositions containing 100 µg ("mcg"; square symbols), 200 µg (triangle symbols) or 500 µg (circle symbols) levothyroxine sodium (1), and either 3 mg (open symbols) or 10 mg (open symbols) mannitol (M).
Figure 3:
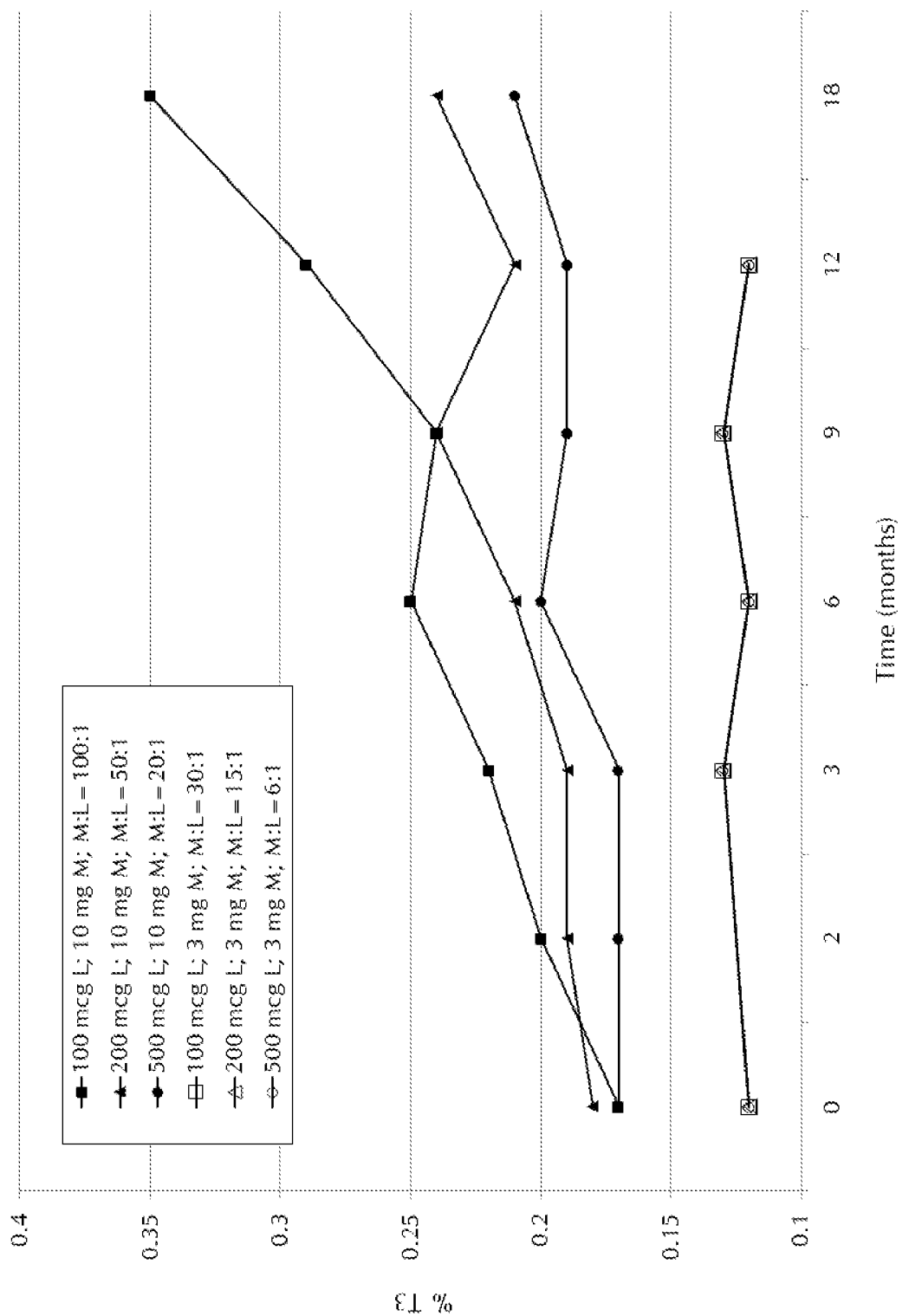
FIG. 3 depicts graphs of the amount of T3 impurity over time at 25° C. for compositions containing 100 µg ("mcg"; square symbols), 200 µg (triangle symbols) or 500 µg (circle symbols) levothyroxine sodium (1), and either 3 mg (open symbols) or 10 mg (open symbols) mannitol (M).

FIG. 2 depicts graphs of liothyronine (T3) impurity over time at 40° C. for compositions containing 100 µg ("mcg"), 200 µg or 500 µg levothyroxine sodium (L), and either 3 mg or 10 mg mannitol (M). FIG. 3 depicts graphs of T3 impurity over time at 25° C. for compositions containing 100 µg, 200 µg or 500 µg levothyroxine sodium, and either 3 mg or 10 mg mannitol. The graphs in FIGS. 2 and 3 for the compositions containing 3 mg mannitol (open symbols) correspond to the results listed in Table 2. The graphs in FIGS. 2 and 3 for the compositions containing 10 mg mannitol (closed symbols) correspond to results of an analysis of the stability of levothyroxine in solid compositions containing 100 µg, 200 µg or 500 µg levothyroxine sodium and 10 mg mannitol. These solid compositions were formed by combining water, the levothyroxine sodium, the mannitol, and 500 µg dibasic sodium phosphate to form liquid mixtures, and then adding sodium hydroxide to provide a pH of about 11.8. Water for injection (USP) was added to each liquid mixture as needed to provide total volumes of 1 mL. The liquid mixtures were lyophilized to provide solid compositions, which were then stored in vials at temperatures of 25° C. or 40° C. The stability of the levothyroxine in the solid compositions over time at different temperatures was determined by measuring the amount of T3, as described above. The results of these measurements for the compositions containing 10 mg mannitol are listed in Table 3, below.

TABLE 3

Stability of levothyroxine in solid compositions containing different amounts of levothyroxine sodium and 10 mg mannitol.

| Levothyroxine Sodium: | 100 µg | 200 µg | 500 µg |
|---|---|---|---|
| Dibasic Sodium Phosphate: | 500 µg | 500 µg | 500 µg |
| Mannitol: | 10 mg | 10 mg | 10 mg |
| M:L ratio: | 100:1 | 50:1 | 20:1 |

| Time (mo.) | Temp (° C.) | % T3 | | |
|---|---|---|---|---|
| 0 | — | 0.17 | 0.18 | 0.17 |
| 1 | 40 | 0.34 | 0.21 | 0.20 |
| 2 | | .030 | 0.23 | 0.21 |
| 3 | | 0.57 | 0.32 | 0.20 |
| 6 | | 0.20 | 0.19 | 0.17 |
| 3 | 25 | 0.22 | 0.19 | 0.17 |
| 6 | | 0.25 | 0.21 | 0.20 |
| 9 | | 0.24 | 0.24 | 0.19 |
| 12 | | 0.29 | 0.21 | 0.19 |
| 18 | | 0.35 | 0.24 | 0.21 |

The results depicted in FIG. 2 show that the solid compositions containing only 3 mg mannitol maintained lower T3 levels at 40° C. over time than did the corresponding compositions containing mannitol at a conventional level of 10 mg. The instability of levothyroxine in compositions containing 10 mg mannitol over time, as indicated by higher T3 levels, was inversely related to the amount of levothyroxine sodium in the compositions. Solid compositions containing 100 µg levothyroxine sodium and 10 mg mannitol (M:L ratio of 100:1) had higher T3 levels over time than did solid compositions containing 200 µg levothyroxine sodium and 10 mg mannitol (M:L ratio of 50:1), which in turn had higher T3 levels over time than did solid compositions containing 500 µg levothyroxine sodium and 10 mg mannitol (M:L ratio of 20:1).

The results depicted in FIG. 3 show that the solid compositions containing only 3 mg mannitol also maintained lower T3 levels at 25° C. over time than did the corresponding compositions containing mannitol at a conventional level of 10 mg. The instability of levothyroxine in compositions containing 10 mg mannitol over time was not as pronounced at 25° C. as it was at 40° C. The inverse relationship between levothyroxine instability and the amount of levothyroxine sodium in these compositions, as described above, was observed from month 2 to month 6.

The results of Tables 1 and 2 and FIGS. 2 and 3 show that the stability of levothyroxine in a solid composition may be improved by lowering the amount of mannitol and/or the mass ratio of mannitol to levothyroxine sodium (M:L) in the composition to a level below that of conventional compositions. Solid compositions containing 100-500 µg levothyroxine sodium and less than 10 mg mannitol may be more stable than solid compositions containing 100-500 µg levothyroxine sodium and a conventional amount of 10 mg mannitol. Solid compositions containing 100-200 µg levothyroxine sodium and having a M:L ratio of 40:1 or lower may be more stable than solid compositions containing 100-200 µg levothyroxine sodium and having a conventional M:L ratio of 50:1 or greater. Solid compositions containing 500 µg levothyroxine sodium and having a M:L ratio of 10:1 or lower may be more stable than solid compositions containing 500 µg levothyroxine sodium and having a conventional M:L ratio of 20:1.

A solid composition that includes levothyroxine sodium and mannitol may be prepared by forming a liquid mixture containing a solvent, levothyroxine sodium, mannitol and optionally one or more other substances, and lyophilizing the mixture. The lyophilizing may include freeze-drying the liquid mixture to provide a solid composition. The liquid mixture may be prepared by combining ingredients including levothyroxine sodium and mannitol in the amounts described above. The liquid mixture may further include a phosphate buffer, a base and/or one or more other substances, as described above.

The liquid mixture may include from 0.1 to 5 mL solvent, from 25 to 1,000 µg levothyroxine sodium, and from 25 µg to 10 mg mannitol. The liquid mixture may include from 0.5 to 2 mL solvent, from 50 to 750 µg levothyroxine sodium, and from 0.1 to 5 mg mannitol. The liquid mixture may include from 0.75 to 1.5 mL solvent, from 50 to 750 µg levothyroxine sodium, and from 1 to 3 mg mannitol. The mass ratio of mannitol to levothyroxine sodium (M:L) in the liquid mixture may be from 1:1 to 40:1, from 5:1 to 35:1, or from 6:1 to 30:1.

The ingredients combined to form a liquid mixture containing a phosphate buffer may include from 0.1 to 5 mL solvent, from 25 to 1,000 µg levothyroxine sodium, from 25 µg to less than 10 mg mannitol, and from 100 to 800 µg dibasic sodium phosphate. The ingredients may include from 0.5 to 2 mL solvent, from 50 to 750 µg levothyroxine sodium, from 0.1 to 7 mg mannitol, and from 200 to 700 µg dibasic sodium phosphate. The ingredients may include from 0.75 to 1.5 mL solvent, from 100 to 500 µg levothyroxine sodium, from 1 to 5 mg mannitol, and from 400 to 600 µg dibasic sodium phosphate. The mass ratio of mannitol to levothyroxine sodium in the liquid mixture may be from 1:1 to 40:1, from 5:1 to 35:1, or from 6:1 to 30:1. Preferably the ingredients are substantially free of tribasic sodium phosphate.

The solvent, levothyroxine sodium, mannitol, optional buffer, optional base and one or more other optional substances may be combined in any order when forming the liquid mixture. For example, a liquid mixture may be formed by adding the levothyroxine sodium and mannitol to a container including the solvent, and then adding a buffer and/or a base to achieve the desired pH in the liquid mixture. The liquid mixture preferably has a pH of from 11 to 12. A presently preferred pH of the liquid mixture is 11.8±0.1.

The solvent in the liquid mixture may include water and/or an organic solvent. If the solvent includes an organic solvent, the organic solvent preferably is miscible with water. Non-limiting examples of organic solvents that are miscible with water and may be present in the solvent include alcohols such as ethanol, isopropanol, and t-butanol. The concentration of organic solvent, if present, may be from 1 to 20 percent by volume (vol %) or from 2 to 10 vol % of the solvent. The liquid mixture may include from 0.1 to 5 mL solvent. Preferably the liquid mixture includes from 0.5 to 2 mL solvent, or from 0.75 to 1.5 mL solvent.

The liquid mixture including the solvent, levothyroxine sodium, mannitol, and any other optional ingredients may be lyophilized to form a solid composition, such as by subjecting the liquid mixture to freeze-drying. Freeze-drying of the liquid mixture may include maintaining the liquid mixture in an inert atmosphere, such as nitrogen or argon. Preferably the liquid mixture is placed in glass vials prior to lyophilization, and the amount of the liquid mixture in each vial is based on the amount of levothyroxine intended to be present in the final solid composition in the vial.

In a typical lyophilization process, the temperature of the liquid mixture is lowered to a temperature at or below the solidification point of the liquid mixture. If the liquid mixture forms a glass when cooled, the solidification point typically is the glass transition temperature. If the liquid mixture forms crystals when cooled, the solidification point typically is the eutectic point. The solidified mixture is then dried under vacuum. Typically, the drying process includes a primary drying step in which the temperature of the solidified mixture is raised gradually while most of the water is removed from the mixture by the vacuum, and a secondary drying step in which the temperature of the solidified mixture is raised further while residual moisture is removed from the mixture by the vacuum. The temperature is kept at or below the desired storage temperature for the final solid composition. Lyophilization typically is complete within 48 hours, but may require additional time. The solid composition resulting from the lyophilization typically is sealed for later use. Details regarding the lyophilization process may be found, for example, in Remington: The Science and Practice of Pharmacy, 20th Ed., ed. A. Gennaro, Lippincott Williams & Wilkins, 2000.

The lyophilized solid composition may be stored for later reconstitution and administration. Preferably the solid composition is stored at a temperature of 10° C. to 40° C., from 15° C. to 35° C., from 20° C. to 30° C., or about 25° C. Preferably the solid composition is protected from light, such as by storing the composition in an opaque or tinted container, such as an amber tinted container. Preferably the solid composition is sealed in a glass vial to protect the composition from moisture in the surrounding environment. Presently preferred containers include amber tinted glass vials.

A solid composition that includes levothyroxine sodium and mannitol may be administered to a patient by combining the composition with an aqueous carrier liquid to form an aqueous mixture, and administering the aqueous mixture into the patient by, for example, injection. Preferably, the aqueous carrier liquid is a pharmaceutically acceptable carrier liquid. Non-limiting examples of pharmaceutically acceptable carrier liquids include water and saline, such as phosphate buffered saline (PBS), Ringers solution or lactated Ringers injection. The aqueous carrier liquid also may include fixed oils, fatty esters or polyols, particularly if the aqueous mixture for injection is a suspension. The aqueous carrier liquid also may include one or more other substances such as buffers, stabilizers, solubilizers, preservatives and antioxidants. Preferably the solid composition dissolves in the aqueous carrier liquid to form a solution. Presently preferred aqueous carrier liquids include sodium chloride injection, such as solutions containing 0.9%, 0.45% or 0.225% sodium chloride. Presently preferred aqueous carrier liquids include 0.9% sodium chloride injection, 0.9% sodium chloride injection USP containing benzyl alcohol, and bacteriostatic sodium chloride injection.

The amount of aqueous carrier liquid may be sufficient to provide an aqueous mixture containing levothyroxine sodium at a concentration of from 5 to 500 μg/mL. Preferably the concentration of levothyroxine sodium in the aqueous mixture is from 10 to 200 μg/mL, or from 20 to 100 μg/mL. Presently preferred concentrations of levothyroxine sodium in an aqueous mixture for injection include about 20 μg/mL, 40 μg/mL and 100 μg/mL.

An aqueous mixture formed from the solid composition may be administered to provide an initial dose of 200-500 μg or of 300-500 μg of levothyroxine sodium to a patient. An aqueous mixture formed from the solid composition may be administered to provide a $2^{nd}$ day dose of 100-300 μg of levothyroxine sodium to a patient. An aqueous mixture formed from the solid composition may be administered to provide a daily dose of 50-100 μg of levothyroxine sodium to a patient. Doses outside of these ranges also may be administered.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A lyophilized solid composition, comprising:
   about 100 micrograms of levothyroxine sodium;
   a buffer; and
   between 2 and 4 milligrams of mannitol.
2. The lyophilized solid composition of claim 1, wherein, when the lyophilized solid composition is stored at 25° C. for a predetermined time period, less than 0.20% of the levothyroxine sodium is converted to liothyronine.
3. The lyophilized solid composition of claim 2, wherein the predetermined time period is 12 months.
4. The lyophilized solid composition of claim 1, wherein about 3 milligrams of mannitol is in the lyophilized solid composition.
5. A pharmaceutical solution, comprising:
   the lyophilized solid composition of claim 1; and
   a pharmaceutically acceptable liquid carrier.
6. The pharmaceutical solution of claim 5, wherein a concentration of the levothyroxine sodium in the pharmaceutical solution is between 5 and 500 μg/mL.
7. A method of providing levothyroxine to a patient in need thereof, the method comprising:
   administering the pharmaceutical solution of claim 5 to the patient in need thereof.
8. The method of claim 7, wherein the pharmaceutical solution is administered to the patient in need thereof such that between about 50 to 500 micrograms of levothyroxine sodium is administered to the patient in need thereof.
9. The method of claim 8, wherein the pharmaceutical solution is administered to the patient in need thereof such that between about 50 to 100 micrograms or about 300 to 500 micrograms of levothyroxine sodium is administered to the patient in need thereof.
10. The lyophilized solid composition of claim 1, wherein the buffer is a phosphate buffer.
11. A lyophilized solid composition, comprising:
    about 200 micrograms of levothyroxine sodium;
    a buffer; and
    between 2 and 4 milligrams of mannitol.
12. The lyophilized solid composition of claim 11, wherein, when the lyophilized solid composition is stored at 25° C. for a predetermined time period, less than 0.20% of the levothyroxine sodium is converted to liothyronine.
13. The lyophilized solid composition of claim 12, wherein the predetermined time period is 12 months.
14. The lyophilized solid composition of claim 11, wherein about 3 milligrams of mannitol is in the lyophilized solid composition.
15. A pharmaceutical solution, comprising:
    the lyophilized solid composition of claim 11; and
    a pharmaceutically acceptable liquid carrier.
16. The pharmaceutical solution of claim 15, wherein a concentration of the levothyroxine sodium in the pharmaceutical solution is between 5 and 500 μg/mL.
17. A method of providing levothyroxine to a patient in need thereof, the method comprising:
    administering the pharmaceutical solution of claim 15 to the patient in need thereof.

18. The method of claim 17, wherein the pharmaceutical solution is administered to the patient in need thereof such that between about 50 to 500 micrograms of levothyroxine sodium is administered to the patient in need thereof.

19. The method of claim 18, wherein the pharmaceutical solution is administered to the patient in need thereof such that between about 50 to 100 micrograms or about 300 to 500 micrograms of levothyroxine sodium is administered to the patient in need thereof.

20. The lyophilized solid composition of claim 11, wherein the buffer is a phosphate buffer.

21. A lyophilized solid composition, comprising:
about 500 micrograms of levothyroxine sodium;
a buffer; and
between 2 and 4 milligrams of mannitol.

22. The lyophilized solid composition of claim 21, wherein, when the lyophilized solid composition is stored at 25° C. for a predetermined time period, less than 0.20% of the levothyroxine sodium is converted to liothyronine.

23. The lyophilized solid composition of claim 22, wherein the predetermined time period is 12 months.

24. The lyophilized solid composition of claim 21, wherein about 3 milligrams of mannitol is in the lyophilized solid composition.

25. A pharmaceutical solution, comprising:
the lyophilized solid composition of claim 21; and
a pharmaceutically acceptable liquid carrier.

26. The pharmaceutical solution of claim 25, wherein a concentration of the levothyroxine sodium in the pharmaceutical solution is between 5 and 500 μg/mL.

27. A method of providing levothyroxine to a patient in need thereof, the method comprising:
administering the pharmaceutical solution of claim 25 to the patient in need thereof.

28. The method of claim 27, wherein the pharmaceutical solution is administered to the patient in need thereof such that between about 50 to 500 micrograms of levothyroxine sodium is administered to the patient in need thereof.

29. The method of claim 28, wherein the pharmaceutical solution is administered to the patient in need thereof such that between about 50 to 100 micrograms or about 300 to 500 micrograms of levothyroxine sodium is administered to the patient in need thereof.

30. The lyophilized solid composition of claim 21, wherein the buffer is a phosphate buffer.

* * * * *